United States Patent [19]
Baker et al.

[11] Patent Number: 5,810,779
[45] Date of Patent: Sep. 22, 1998

[54] FLUID ADMINISTRATION

[75] Inventors: Tony James Baker, Highwoods; Roland Henry Clyne Carter, Hythe, both of England

[73] Assignee: Smiths Industries PLC, London, England

[21] Appl. No.: 764,470

[22] Filed: Dec. 12, 1996

[30] Foreign Application Priority Data

Dec. 14, 1995 [GB] United Kingdom .................. 9525562

[51] Int. Cl.$^6$ .................................................. A61M 1/00
[52] U.S. Cl. ......................................... 604/151; 604/218
[58] Field of Search ................................. 604/131, 149, 604/151, 207, 208, 218, 211, 215

[56] References Cited

U.S. PATENT DOCUMENTS

| | | | |
|---|---|---|---|
| 4,282,867 | 8/1981 | Du Toit | 604/151 X |
| 4,411,651 | 10/1983 | Schulman | 604/151 |
| 4,828,551 | 5/1989 | Gertler et al. | |
| 5,378,231 | 1/1995 | Johnson et al. | 604/151 X |
| 5,383,858 | 1/1995 | Reilly et al. | 604/151 X |

FOREIGN PATENT DOCUMENTS

WO 90/12609  11/1990  WIPO .

*Primary Examiner*—Max Hindenburg
*Assistant Examiner*—Pamela Wingood
*Attorney, Agent, or Firm*—Pollock, Vande Sande & Priddy

[57] ABSTRACT

A PCA pump has a fluid reservoir connected via a capillary and a gas vent filter to a cylinder having a piston urged outwardly by a spring to draw fluid into the cylinder. A button can be pressed by the user to press in the piston and dispense fluid. After actuation, the piston moves out to fill the cylinder with fluid and the button is disconnected from the piston until it has moved back to its outer position.

9 Claims, 3 Drawing Sheets

FLUID ADMINISTRATION

BACKGROUND OF THE INVENTION

This invention relates to apparatus for the administration of fluid.

The invention is more particularly concerned with apparatus for administrating drugs or other medicaments to a patient.

Various apparatus are available that enable patients safely to administer doses of intravenous medication at will, without the need for medical staff. The apparatus can enable the medication to be given when needed most and can often result in a reduction in the amount of drug used. Previous apparatus have provision for preventing the patient exceeding a safe dose. This can be achieved readily in electronically-controlled apparatus but these are relatively expensive and not suited for single-use application. Various forms of low-cost, mechanical apparatus have been proposed, such as described in WO93/00944, WO88/02637. WO91/08002, WO95/08359, WO88/00841, FR2215246, FR2338710, EP32792, EP483759, U.S. Pat. No. 4,201,207, U.S. Pat. No. 3,035,575, U.S. Pat. No. 4,828,551 and "Patient-Controlled Analgesia" by Rapp et al., DICP The Annals of Pharmacotherapy, 1989 November, vol 23, p 899. These mechanical apparatus usually prevent overdosing by means of a flow restrictor so that, even if the patient were to actuate the apparatus repeatedly at short intervals, the restrictor would prevent the safe dose being exceeded. While such apparatus can effectively prevent overdosing, they can allow the patient to administer low doses of medication at frequent intervals so that there is an almost continuous administration. With some medication, this can be an advantage or not a significant problem. However, with other medication, most notably analgesics, it is an advantage for the medication to be given less frequently, in larger amounts, as boluses.

SUMMARY OF THE PRESENT INVENTION

It is an object of the present invention to provide an improved fluid administration apparatus.

According to one aspect of the present invention there is provided fluid administration apparatus including a fluid reservoir, a fluid chamber of variable volume having an inlet and an outlet, the inlet being connected with the reservoir via an inlet fluid passage and the outlet being connected with an outlet fluid supply passage by which fluid can be supplied to a patient, the fluid chamber including an actuator that is movable from a first position in which the fluid chamber has a first volume to a second position in which the fluid chamber has a second volume less than the first volume so that fluid is pumped from the chamber to the fluid supply passage, and the apparatus including a user-actuable member coupled with the actuator, the user-actuable member being actuable by the user to dispense fluid only when the actuator is in its first position.

The apparatus preferably includes means to retain the user-actuable member in an actuated position after actuation until the actuator has returned to the first position. The user-actuable member is preferably a button extending over the actuator, the button and actuator being locked together when the button is pressed in to pump fluid from the chamber, the button being locked in its actuated position, the actuator being unlocked from the button when the actuator reaches its second position such that the actuator can be displaced out independently of the button, and the button being unlocked from its actuated position by displacement of the actuator to its first position. The fluid chamber may be a cylinder and the actuator may include a piston. The reservoir may include a cylinder having a piston movable along its length, the apparatus having an inlet opening into the cylinder on one side of the piston, and the inlet fluid passage opening into the cylinder on the one side. The inlet fluid passage preferably includes a filter opening externally of the apparatus that allows the escape of gas but prevents the escape of liquid. The inlet fluid passage preferably includes a capillary arranged to restrict the flow of fluid into the chamber. The fluid chamber may include a resilient member operable to displace the actuator from the second to the first position. The fluid chamber may be located alongside the reservoir and the outlet fluid flow passage may extend substantially parallel to the reservoir.

Medical infusion pump apparatus for patient-controlled analgesia according to the present invention, will now be described, by way of example, with reference to the accompanying drawings.

DETAILED DESCRIPTION OF THE PREFERRED EMBODIMENT

Figure 1:
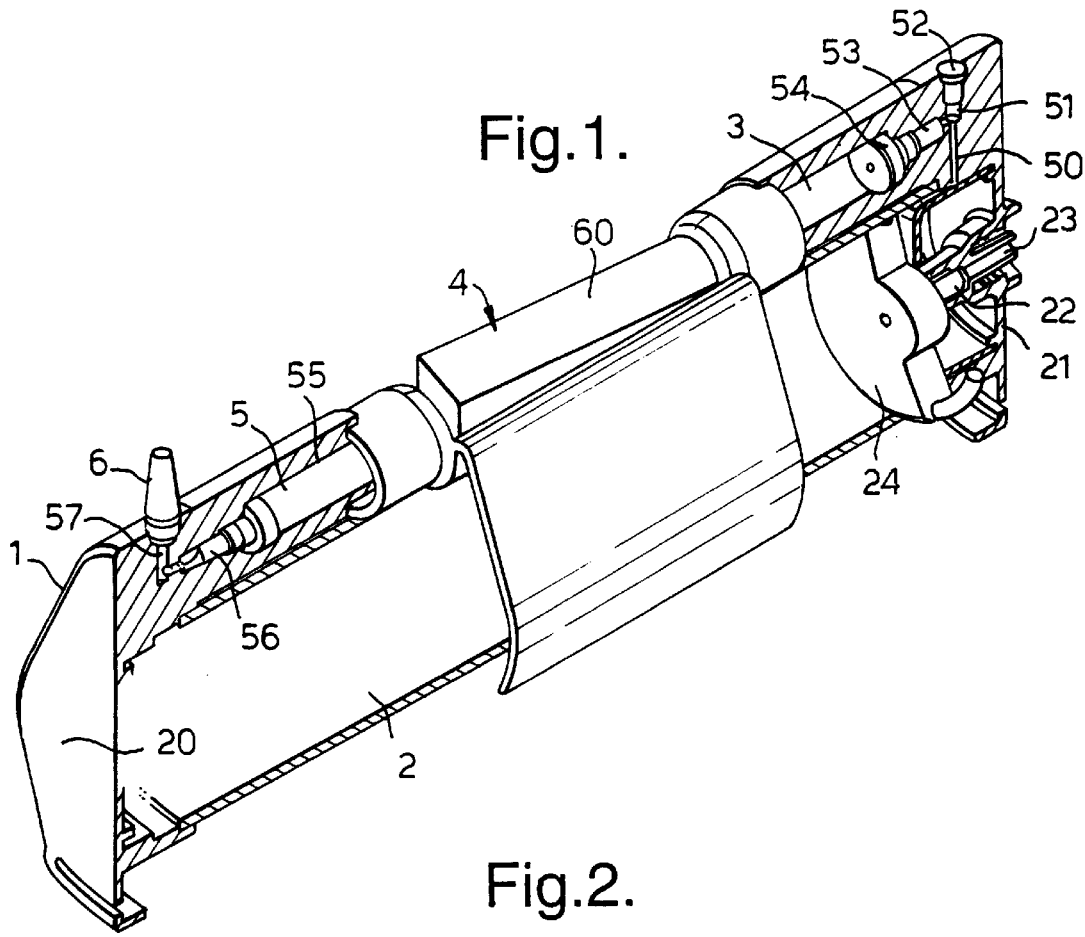
FIG. 1 is a cut-away perspective view of the apparatus.

With reference first to FIG. 1, the pump apparatus has a tubular housing 1 including a fluid reservoir 2 connected via an inlet fluid passage 3 to the inlet of a pump assembly 4. The outlet of the pump assembly 4 is connected via an outlet fluid supply passage 5 to a coupling 6 on the housing. In use, the coupling 6 is connected to a catheter or cannula extending to the patient for administration of the drug contained in the reservoir 2.

The fluid reservoir 2 is of circular section with a volume of about 60 ml. The left-hand end 20 of the reservoir 2 is closed; the right-hand end 21 has a one-way valve 22 with a female luer tapered inlet entrance 23 in which the nose of a syringe (not shown) can be inserted. A piston 24 is movable along the reservoir 2 in either direction, the piston forming a sliding seal around its periphery with the inside surface of the reservoir.

The fluid passage 3 opens at one end into the right-hand end of the reservoir 2. The passage 3 comprises a first portion 50, of relatively small diameter, extending radially outwards to the upper edge of the housing 1 where it opens into a small recess 51. The recess 51 opens at the surface of the housing 1 but is plugged by a hydrophobic filter 52, which allows gas to escape but prevents the passage of liquid. A second portion 53 of the passage extends from the recess 51, below the filter 52, and extends longitudinally parallel to the reservoir 2. A capillary insert 54 is located in the second portion 53 of the passage to limit flow along the fluid passage to about 0.1 ml/min. The left-hand end of the second portion 53 of the passage 5 opens into the inlet of the pump assembly 4, which will be described in detail below. On the left-hand end of the pump assembly 4, the fluid passage 5 continues as a third, outlet portion 55, which is connected to the coupling 6 via a one-way valve 56 and a short radially-extending fourth portion 57.

Referring now to FIGS. 2 to 5, the pump assembly 4 has a fluid chamber 40 in the form of a vertical cylinder. At its lower end, the chamber 40 has an inlet 41, connected to the second portion 53 of the fluid passage 5, and an outlet 42 connected to the third portion 55 of the fluid passage. An actuator piston 43 is located in the cylinder 40 and is movable along its length, up or down, to vary the volume of the chamber. A spring 44 urges the piston 43 towards the upper end of cylinder 40, that is, so that the volume of the chamber defined below the piston tends to increase. The piston 43 is connected, above the chamber 40, to a horizontally-extending striker arm 45. At its right-hand end, the arm 45 has a locking cam 46 pivoted about a horizontal axis. The left-hand end 47 of the striker arm 45 extends to a button lock 48. The striker arm 45 is concealed below a user-actuable member or button 60.

The button 60 is pivoted about the same horizontal axis as the striker arm 45, towards its right-hand side. At the lower edge of the button 60, on its right-hand side, a pawl lever 61 is pivotally mounted about a horizontal axis and is urged in an anti-clockwise direction by a spring 62 so that a tooth 63 at the upper end of the lever engages a detent 64 formed in the locking cam 46. At its left-hand side, the button 60 has a catch member 65 projecting downwardly within the button lock 48. The button lock 48 is of U-shape with two upwardly-projecting arms 66 and 67, each having a tooth 68 and 69 respectively projecting to the right. The button lock 48 is pivoted about a horizontal axis midway along the length of the left-hand arm 66 and is urged clockwise by a spring 70. The tooth 68 of the left-hand arm 66 is positioned to cooperate with the catch member 65, whereas the tooth 69 on the right-hand arm 67 is positioned to cooperate with the left-hand end 47 of the striker arm 45.

The pump apparatus is filled with medication liquid by means of a syringe (not shown), the nose of which is mated with the entrance 23. As the plunger of the syringe is depressed, the increased pressure opens the valve 22 allowing fluid to enter the reservoir 2 on the right-hand side of the piston 24. The piston 24 moves to the left as fluid is introduced. Any gas in the reservoir 2, to the right of the piston 24 escapes via the passage 5 and the hydrophobic filter 52.

Figure 2:
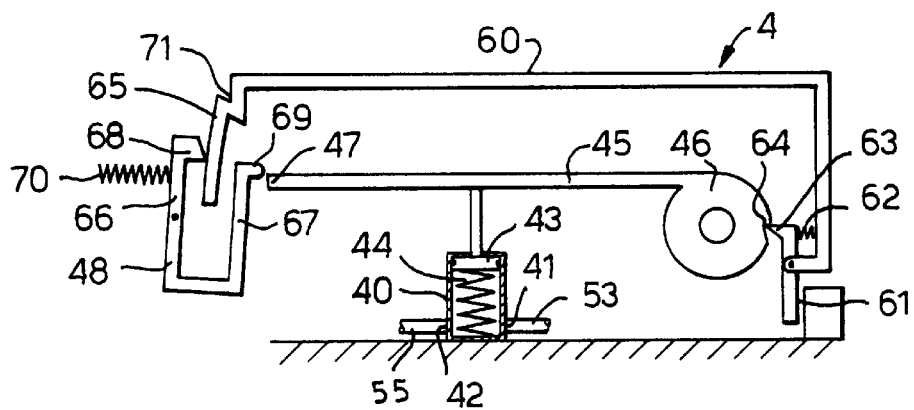
FIGS. 2 to 5 are schematic sectional views of the pump assembly of the apparatus at four different stages of operation.

Initially, with the pump assembly 4 in its unactuated state, as shown in FIG. 2, the spring 44 in fluid chamber 40 urges the piston 43 upwardly so that the chamber has its maximum volume and is full of liquid. In this state, the tooth 63 on the pawl lever 61 engages the detent 64 on the cam 46, so the button 60 is maintained in its upper position with the catch member 65 disengaged from the button lock 48.

Figure 3:
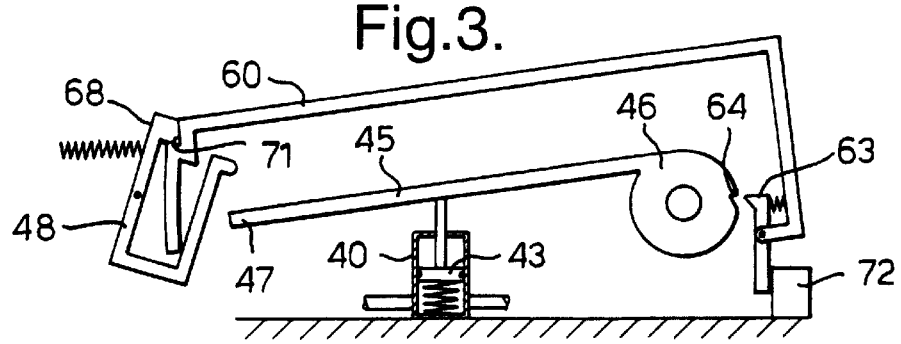
Figure 4:
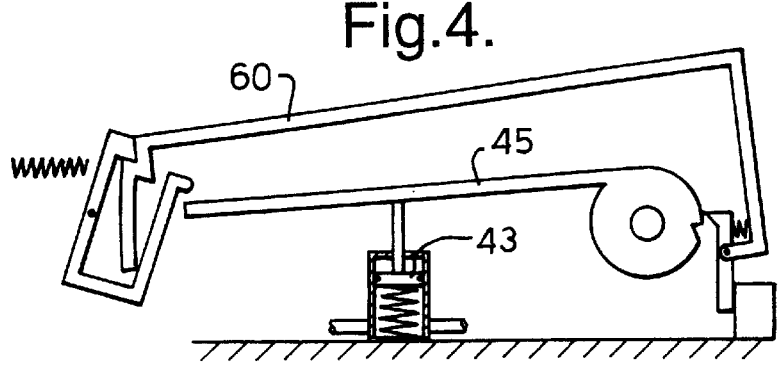
Figure 5:
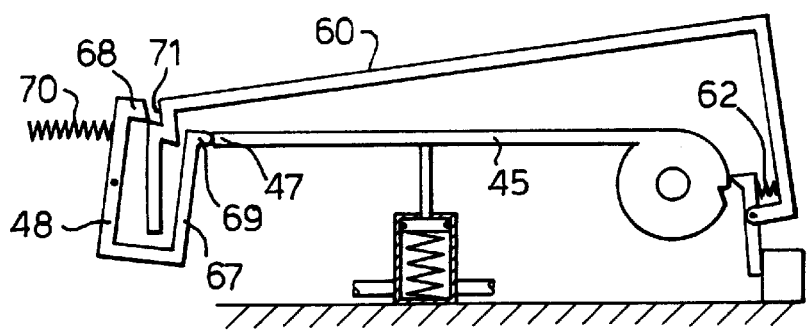

When the user needs a dose of medication, he pushes down on the upper surface of the button 60 causing it rotate about its pivot and move down at its left-hand end. As this happens, the engagement of the pawl lever 61 with the locking cam 46 will also cause the striker arm 45 to rotate about its pivot point and move down at its left-hand end 47. This in turn causes the piston 43 to move down the chamber 40, thereby reducing the effective volume of the chamber and causing all the fluid in the chamber to be pumped out through the outlet 42 to the coupling 6 via the third portion 55 of the fluid passage. The capillary insert 54 prevents any significant flow of fluid out of the inlet 41 of the chamber. The button 60 moves down until the tooth 68 on the button lock 48 engages in a notch 71 on the catch member 65, as shown in FIG. 3. When the button 60 reaches this position, the lower end of the pawl lever 61 contacts a fixed stop 72, which brings the tooth 63 out of engagement with the detent 64 and, therefore, disengages the striker arm 45 from the button 60. The striker arm 45 is now free to be displaced up by the spring 44, through the positions shown in FIGS. 4 and 5, to its original position while the button 60 is locked down so that further actuation by the user is not possible. The rate at which the striker arm 45 can move up is limited by the flow rate through the capillary 54. Typically, the capacity of the chamber 40 is 0.4 ml so, with a flow rate through the capillary of 0.1 ml/min, it would take 4 to 5 minutes for the chamber to fill again and resume the position shown in FIG. 5. As the left-hand end 47 of the striker arm 45 moves up past the tooth 69 on the arm 67 of the button lock 48, it will cause the lock to move anti-clockwise, against the action of its spring 70, thereby displacing the tooth 68 to the left, away from the notch 71 in the catch member 65. This releases the button 60, allowing the spring 62 to rotate it in a clockwise sense upwardly to its rest position, shown in FIG. 2. In this state, the button 60 can again be actuated by the user to administer another dose of medication.

Each time that the fluid chamber 40 is filled with fluid from the reservoir 2, the piston 24 moves a small distance to the right as the volume in the reservoir reduces. In the apparatus described above, fluid is drawn into the fluid chamber 40 by the action of its spring 44. Alternatively, the reservoir 2 could have a spring urging its piston 24 to the right, so that fluid is pumped out of the reservoir into the fluid chamber.

The apparatus of the present invention has the advantage that it is of a simple mechanical construction that can be made cheaply enough to be disposable while ensuring that medication can only be given as boluses spaced apart in time.

Figure 6:
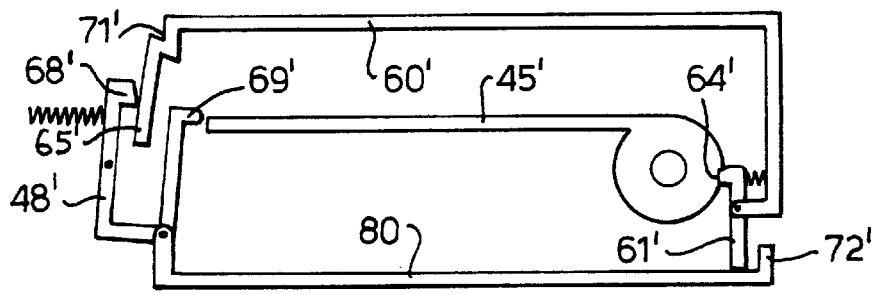
FIGS. 6 and 7 are schematic sectional views of an alternative pump assembly at two different stages of operation.
Figure 7:
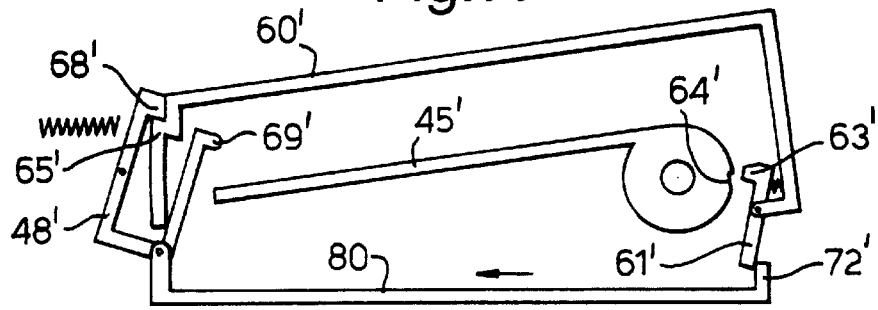

There are various alternative ways in which apparatus according to the invention could be constructed. FIGS. 6 and 7 show alternative apparatus having some components similar to the apparatus shown in FIGS. 2 to 5, which are given the same numbers primed. The fluid chamber is omitted, for clarity. In the apparatus of FIGS. 6 and 7, the fixed stop 72 of the previous apparatus is replaced by a movable stop 72' at one end of a horizontal slider 80. The other end of the slider 80 is coupled to the button lock 48' at a point on the opposite side of its pivot point from the tooth 68'. When the button 60' is depressed, the catch member 65' moves down until the tooth 68' on the button lock 48' can engage the notch 71' on the catch member. When this happens, it can be seen that the button lock 48' will rotate clockwise; this in turn pulls the slider 80 to the left and, with it, the stop 72'. As the stop 72' moves to the left, it contacts the lower end of the pawl lever 61' moving this clockwise so that its tooth 63' comes out of engagement with the detent 64'. This allows the striker arm 45' to move up to its original position. When the striker arm 45' contacts the tooth 69' on the lock 48', it releases the button 60' so that this can be actuated again.

Figure 8:
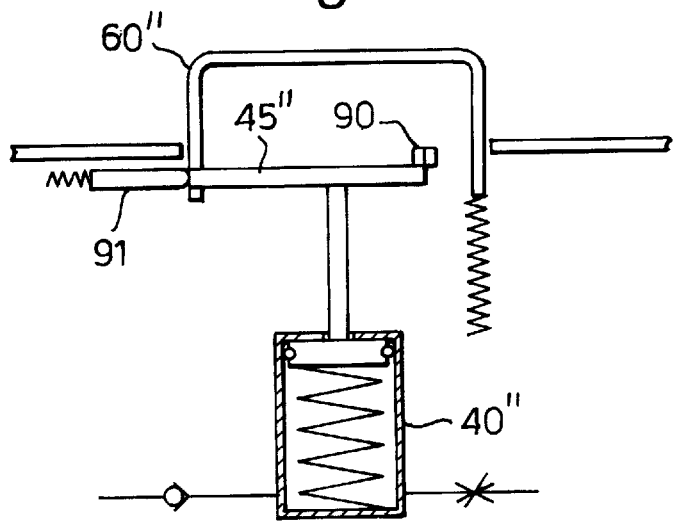
FIGS. 8 to 10 are schematic sectional views of a further alternative pump assembly at three different stages of operation.
Figure 9:
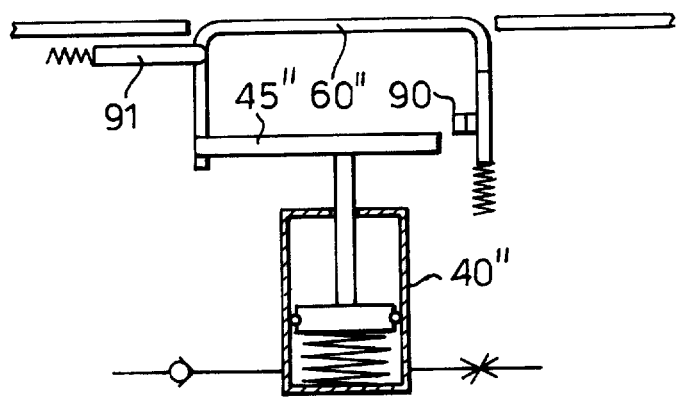
Figure 10:
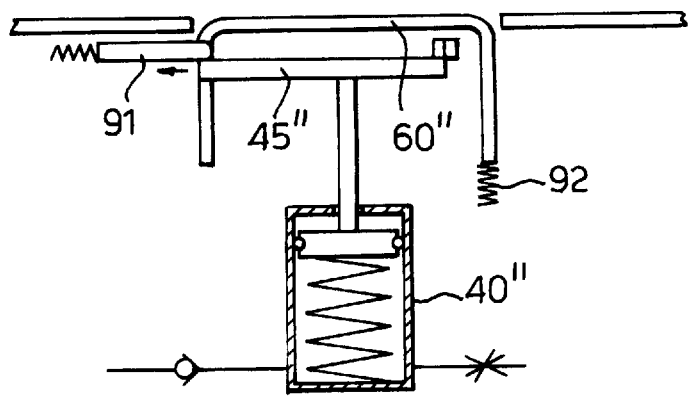

Further alternative apparatus is shown in FIGS. 8 to 10 in which similar components to those in the apparatus described above have the same reference numeral, which is double primed. In this arrangement, the button 60" and striker arm 45" are both movable vertically up and down. In the rest position shown in FIG. 8, the striker 45" is retained with the button 60" by a lock 90 so that, as the button is depressed, the striker arm is also depressed. When the button 60" reaches the lower extent of its travel, as shown in FIG. 9, the lock 90 is released, allowing the striker arm 45" to move upwardly relative to the button as the fluid chamber 40" fills with fluid. The button 60", however, is retained in its depressed position by a second lock 91 until the striker 45" has moved fully upwardly to the position shown in FIG. 10 where it releases the second lock 91 and allows the button to move upwardly to its original position under the action of a return spring 92.

What we claim is:

1. Fluid administration apparatus comprising: a fluid reservoir; a fluid chamber of variable volume having an inlet and an outlet; an inlet fluid passage connecting said inlet with said reservoir; an outlet fluid passage connected with said outlet by which fluid can be supplied to a patient; an actuator that is movable from a first position in which the fluid chamber has a first volume to a second position in which the fluid chamber has a second volume less than the first volume so that fluid is pumped from the chamber to said outlet fluid passage; a user-actuable member coupled with said actuator; and a member for retaining said user-actuable member in an actuated position after actuation, said retaining member being engaged and released by said actuator when said actuator is in said first position, such that said user-actuable member is actuable by the user to dispense fluid only when said actuator is in its first position.

2. Fluid administration apparatus according to claim 1, wherein said user-actuable member is a button extending over said actuator, wherein said button and actuator have cooperating catches that lock the button and actuator together when said button is pressed in to pump fluid from the chamber, wherein said button is locked in its actuated position, wherein said actuator is unlocked from said button when the actuator reaches its second position such that said actuator can be displaced out independently of the button, and wherein said button is unlocked from its actuated position by displacement of said actuator to its first position.

3. Fluid administration apparatus according to claim 1, wherein said fluid chamber is a cylinder and said actuator includes a piston.

4. Fluid administration apparatus according to claim 1, wherein said reservoir includes a cylinder having a piston movable along its length, the apparatus having an inlet opening into said cylinder on one side of said piston, and said inlet fluid passage opening into said cylinder on the said one side.

5. Fluid administration apparatus according to claim 1, wherein said inlet fluid passage includes a filter opening externally of the apparatus that allows the escape of gas but prevents the escape of liquid.

6. Fluid administration apparatus according to claim 1, wherein said inlet fluid passage includes a capillary arranged to restrict the flow of fluid into said chamber.

7. Fluid administration apparatus according to claim 1, wherein said fluid chamber includes a resilient member operable to displace said actuator from said second to said first position.

8. Fluid administration apparatus according to claim 1, wherein said fluid chamber is located alongside said reservoir and said outlet fluid flow passage extends substantially parallel to said reservoir.

9. A pump comprising: a fluid reservoir; a fluid chamber having an inlet and an outlet; an inlet fluid passage connecting said inlet with said reservoir; a capillary in said inlet fluid passage restricting flow of fluid to said chamber; an outlet fluid passage connected with said outlet by which fluid can be supplied to a patient; a piston that is movable along said fluid chamber from a first position in which the fluid chamber has a first volume to a second position in which the fluid chamber has a second volume less than the first volume so that fluid is pumped from the chamber to said outlet fluid passage; a resilient member for displacing said piston from said second position to said first position and drawing fluid from said reservoir into said cylinder; a button movable between a first position and a second, actuated position; a spring acting on said button to urge said button to said first position; a coupling between said button and said piston, said coupling being engaged during movement of said button from said first to said second position such that said piston is moved with said button from said first to said second position, said coupling being disengaged when said button reaches said second position such that said piston can return to said first position independently of said button; and a lock arranged to engage said button in said second position and to be engaged and released by said piston when said piston is in said first position, said lock retaining said button in said second position until said lock is released by engagement with said piston when said piston returns to said first position whereupon said spring is operable to displace said button back to said first position.

\* \* \* \* \*